United States Patent [19]

Allmendinger

[11] 4,432,656
[45] Feb. 21, 1984

[54] PROCESS FOR MONITORING THE HISTORY OF TEMPERATURE VERSUS TIME OF DEEP-FROZEN PRODUCT, INDICATOR FOR APPLYING SAID PROCESS AND UTILIZATION OF SAID PROCESS

[76] Inventor: Thomas Allmendinger, Bruggwiesenstr. 7, 8152 Glattbrugg, Switzerland

[21] Appl. No.: 253,748

[22] PCT Filed: Jul. 11, 1980

[86] PCT No.: PCT/CH80/00085
§ 371 Date: Mar. 12, 1981
§ 102(e) Date: Mar. 12, 1981

[87] PCT Pub. No.: WO81/00303
PCT Pub. Date: Feb. 5, 1981

[30] Foreign Application Priority Data
Jul. 13, 1979 [CH] Switzerland ............... 6535/79

[51] Int. Cl.³ ................. G01K 3/04; G01K 11/16
[52] U.S. Cl. ......................... 374/102; 116/206; 116/216; 426/88
[58] Field of Search .............. 116/216, 219, 206; 73/356, 357; 426/88; 374/102, 106, 162

[56] References Cited

U.S. PATENT DOCUMENTS

| 2,552,477 | 5/1951 | Cole | 374/102 |
| 2,762,711 | 9/1956 | Zopf | 116/206 |
| 3,615,719 | 10/1971 | Keller et al. | 426/88 |
| 3,620,677 | 11/1971 | Morison | 116/206 |
| 3,695,903 | 10/1972 | Hahn et al. | 116/216 |
| 3,946,611 | 3/1976 | Larsson | 116/216 |
| 4,137,049 | 1/1979 | Couch et al. | 116/206 |
| 4,154,107 | 5/1979 | Grozen et al. | 374/102 X |

FOREIGN PATENT DOCUMENTS 1604649 12/1981 United Kingdom ............... 116/216

Primary Examiner—Jerry W. Myracle
Assistant Examiner—Tom Noland
Attorney, Agent, or Firm—Lawrence Rosen

[57] ABSTRACT

The disclosure concerns an indicator for providing a time/temperature integrated indication of the temperature history of a deep-frozen product through the diffusion of water along a cellulose wick. The cellulose wick is provided on itself with a water soluble, hydrate forming substance, such as sodium chloride and citric acid. The wick is covered in a plastic covering with an opening in the covering exposing the wick to water at the product, and the advance of the water front along the wick is indicated by a time/temperature indicator adjacent the wick and/or by an acid/base indicator on the wick and spaced from the indicator.

15 Claims, 8 Drawing Figures

PROCESS FOR MONITORING THE HISTORY OF TEMPERATURE VERSUS TIME OF DEEP-FROZEN PRODUCT, INDICATOR FOR APPLYING SAID PROCESS AND UTILIZATION OF SAID PROCESS

BACKGROUND OF THE INVENTION

The present invention relates to a method of monitoring the history of temperature versus time of a deep-frozen product in the way of a time integral of its temperature development, with an indicator for sensing the course of diffusion of water in a path of diffusion; and relates to an indicator for carrying out said method and to the utilization of said method.

STATE OF THE ART

There has been a need for a long time to monitor deep-frozen foodstuffs. Reference is made in this respect to U.S. patent specification Ser. No. 1,535,536 dating back to the year 1925, which relates to the monitoring of the storage temperature of ice cream. This published document was followed by a number of others relating to overcoming as to how the uncertainty with respect to the storage temperature of deep-frozen products with the help of a simple and inexpensive indicator. Attention is called in this regard to the publication by H. M. Schön and C. H. Byrne in "FOOD TECHNOLOGY", October 1972, in which relevant publications are listed in a summarized form. Most conventional indicators are based on the principle comprising the monitoring of a limit temperature on the deep-frozen products by indicating any, even though only brief exceeding of said limit temperature either immediately or with some delay within the order of magnitude of hours. Such indicators are known as "defrost indicators". Said indicators function in most cases on the principle that a liquid, which is in the frozen state at the required storage temperature, melts if the limit temperature is exceeded above $-18°$ C., and the liquid is absorbed by a wick or strip of paper, and subsequently flows to an indicating field where it causes a color change. Reference is made in this connection, for example to French patent specification No. 1,548,424, or U.S. Pat. No. 2,951,764.

However, the durability of deep-frozen products has been investigated more recently in greater detail. It was found that specific critical temperatures do not exist, but that the permissible storage time of deep-frozen products is rather reduced continuously as the temperature increases, namely with a quality reduction that takes place approximately logarithmically. It has become a customary procedure to show graphically by means of so-called durability curves the periods after which an acceptable quality limit can be still achieved as a function of the temperature. FIG. 1 shows a number of durability curves for various types of product, which are borrowed from the publication "Recommandations pour la préparation et la distribution des aliments congelés", 2nd edition, 1972, pages 118/119, published by the "Institut International du Froid", Paris.

Said durability curves vary for different product categories, and both the maximum permissible storage duration at $-20°$ C. and the storability as a function of the temperature may be different. Normally, the frequency of the temperature fluctuations plays a negligible role, with the exception of ice cream. More recently, it has become customary to use for the durability of deep-frozen products as a function of the temperature the so-called $Q_{10}$-value. This is the quotient which is obtained by dividing the duration of durability of a specific product at a defined temperature by the duration of durability of said product at a temperature that is $10°$ C. higher. However, since said $Q_{10}$-value depends on the temperature, which means, for example, that its value in the range of $-2.5°$ C. and $-12.5°$ C. is different from the one in the range of $-10°$ C. and $-20°$ C., the $Q_{-20°/-2.5°}$ C.-value is introduced in the present case instead of the $Q_{10}$-value for the characterization of the function of the temperature, the former covering the storage temperature range of $-20°$ C. and $-2.5°$ C. that is of interest to deep-frozen products just prior to thawing.

According to a rough classification the $Q_{-20°/-2.5°}$ C.-values are as follows: for vegetables and fruits about 45; for meat and fish about 20. Other product categories fall within said extreme cases.

Now, with indicators which have become known more recently, the reaching of a quality limit characteristic of a deep-frozen product in dependency on the temperature is indicated in a way corresponding with the durability curve of said product. This is achieved by permitting a liquid to diffuse upwardly in a strip, namely the more rapid the diffusion the higher the temperature rise within the environment of said strip. If such a strip is incorporated in a deep-frozen product shortly prior to the freezing of said product, said strip picks up or senses all changes occurring in the future, which is reflected by the liquid starting to flow more rapidly if the temperature should occasionally increase, and subsequently again more slowly when the temperature drops. Since this action is irreversible, all reductions in quality due to temperature rises are integrated. Such indicators are known under the term "time temperature integrator". Reference is made in this regard to the following publications:

A. Kramer and J. W. Farquahr: "Testing of Time-Temperature Indicating and Defrost Devices", FOOD TECHNOLOGY, February 1976, pp. 5+-56;

C. H. Byrne: "Temperature Indicators-the State of the Art", FOOD TECHNOLOGY, June 1976, pp. 66-68;

H. Schubert: "Indikatoren zur Kontrolle der Zeit-Temperatur-Belastung von tiefgefrorenen Lebensmitteln" (Indicators for Controlling the Time-Temperature Load of Deep-Frozen Foodstuffs), Zeitschrift für Lebensmittel Technologie und Verfahrenstechnik, 31(3): 137-142, 1980.

(this article, however, was published only after the date of our original application in Switzerland).

In this conjunction, particular reference must be made to U.S. Pat. No. 3,946,611. Whereas in certain embodiments it is mainly an aqueous solution that constitutes the supply of diffusion fluid used for such defrost indicators (for example, French Pat. No. 1 548 424, U.S. Pat. No. 3,414,415, DE Pat. No. 2 130 926), the U.S. Pat. No. 3,946,611 makes provision for a gas-absorbing substance along the diffusion path. True, the possibility of utilizing water vapor as the gas is referred to, but there is no further discussion as to the substances that might come into consideration as absorbents in such a case. According to this patent, moreover, the path of diffusion on the indicator is separated by a semipermeable foil from the fluid supply provided on the indicator. Along with the relatively complex configuration necessitated by the semipermeable foil and the fluid supply to be provided on the indicator, this indicator has the drawback because of the semipermeable foil, that the diffusion velocity is reduced at a time when the fluid supply melts, in other words, in the presence of water, when the zero-degrees centigrade barrier is surmounted. Yet, it is precisely at this point that accelerated diffusion is desirable.

SUMMARY OF THE INVENTION

The present invention proposes a process for monitoring the history of time versus temperature of deep-frozen products in the way of a time integral of its temperature development. It uses an indicator for sensing the development of the diffusion of water in a path of diffusion. By this process, furthermore, the reaching of a quality limit characteristic of a deep-frozen product as a function of the temperature is indicated in a way such that it corresponds with the durability curve of said product. The process avoids the drawbacks of providing a semipermeable foil between the water and the path of diffusion, and also the complicated arrangement of a liquid reserve, in particular of a water reserve on the indicator.

The process achieves this by activating the indicator by contacting the path of diffusion of said indicator with water of the product, which may be the moisture content of the product itself or an additionally provided water or ice reserve.

An indicator for carrying out said process is characterized by using as the path of diffusion a body provided with a water-soluble, hydrate-forming substance, or with a mixture of substances, said body being wrapped in a moisture-tight cover except for a point for contacting the water.

Said moisture-tight wrapping is provided because the body, with the exception of the contacting point, may not absorb any moisture. By not providing a semipermeable foil that separates the path of diffusion from the water reserve the rate of diffusion increases significantly as soon as the water reserve starts to melt, thus as soon as the 0° C.-limit is exceeded. This additional effect is practically lost when using a semipermeable membrane. If one uses as the water or ice reserve not pure water but, instead, for example, ice cream, this results in additional effects bearing favorably upon the indication, because the larger the proportion of dissolved substances in the water reserve the more rapid the diffusion of the liquid front in the path of diffusion. This effect correlates positively with the fact that fruit glacé, which has much sugar, is also less durable than the cream glacé with low sugar content.

In the simplest case, for example with meat packaged in a clear, shrunk-on foil material, or with glacé, it is possible to make use of the moisture content of the product itself that has to be monitored. In other cases, it is necessary to provide the packaging material of the product with a small cavity for receiving a small amount of water. Contrary to providing a water reserve on the indicator this assures also that no premature, undesired activation of the indicator can take place.

The indicator is provided in a particularly simple embodiment by a cellulose body, preferably an absorbent paper.

The treatment of the path of diffusion or body is of decisive importance for obtaining the desired indication. Normally, it is felt that it will be necessary to apply to said body a substance that is known to be hygroscopic, for example such as calcium chloride, sodium hydroxide, phosphorous pentoxide etc., i.e. a substance capable of absorbing moisture from the air. However, it was found that such highly hygroscopic substances result in an only low temperature dependency of the diffusion rate of water, which means that said substances permit only the sensing of very low $Q_{-20°/-2.5°}$ C.-values. Also, most of said substances are not harmless with respect to foodstuff hygiene, which is a very important criterion in this connection.

Based on the knowledge that at 100% relative air humidity any water-soluble substance becomes hygroscopic due to the compensation in the concentration which occurs, and that the liquid front becomes clearly visible in the path of diffusion only if the substance serving for the absorption forms a hydrate, it was found that the water-soluble, hydrate-forming substance is preferably sodium chloride, citric acid, a sugar, cobaltous chloride, or a mixture of two or a plurality of said substances. With said substances, which are inexpensive and, with the exception of cobaltous chloride, harmless with respect to foodstuff hygiene, it is possible to achieve very high $Q_{-20°/-2.5°}$ C.-values such as, for example of up to 50, using a citric acid/sodium chloride mixture. Below the cryohydric point, which for sodium chloride lies at about $-22°$ C. and for citric acid at approximately $-15°$ C., and for mixtures is slightly lower, the action of absorption and diffusion comes to a standstill, because the substances are then no longer water-soluble.

While it was found that a citric acid/sodium chloride mixture is particularly suitable for monitoring most deep-frozen products, the use of pure citric acid is recommended for monitoring glacé.

Also cobaltous chloride or cobaltous chloride in mixture with sodium chloride and sugar would be suitable to the extent that in this case, the absorption of water takes place combined with a clearly visible color change from blue to red. However, the $Q_{-20°/-2.5°}$ C.-values achievable with such a mixture of substances are comparatively low; furthermore, cobaltous chloride is neither non-toxic nor inexpensive.

It is proposed, furthermore, to provide along the body of the indicator a time scale for indicating the remaining durability of a product to be monitored at a specific temperature, preferably at $-20°$ C. Furthermore, it is proposed to provide on the body an acid/base indicator, preferably litmus paper, for indicating a predetermined diffusion limit value, and to apply to the body a water-soluble acid, preferably citric acid, or a base, which is dissolved by the diffusing water and carried to the acid/base indicator. This divides the field of indication into two zones. The first zone is formed by the logarithmic time scale provided along the path of diffusion indicating the remaining durability of the product to be monitored at a specific temperature, preferably at $-20°$ C. as stated above. Within said zone, indication takes place in the form of the aqueous front advancing by diffusion. In the second zone, when a predetermined path limit value is reached this is indicated by the color change of the acid/base indicator: an acid or a base, and preferably citric acid originally present on the body in the solid state, is dissolved by the diffusing water and carried to the acid/base color indicator. Therefore, the color change taking place on said indicator tells the consumer that the monitored product has reached a defined quality limit.

If the path of diffusion is provided with a sodium chloride/citric acid mixture, the indicator, for example litmus paper, is subject to a premature, undesirable color change, namely from blue to red, while the nonactivated indicator is being stored because it is assumed that the above mixture may form a small amount of hydrochloric acid which is diffused to the litmus paper.

In order to prevent said premature color change it is proposed to separate the body—if it is provided in its path of diffusion with a sodium chloride/citric acid mixture—from the acid/base color indicator by means of a section of path provided with an acid ampholyte, preferably with secondary ammonium citrate. The buffer zone so formed absorbs the undesired hydrochloric gas by virtue of its basic properties.

Since it is unavoidable in some cases for practical reasons to already bring the indicator into contact with the water reserve shortly before the water has frozen, for example if water is filled first into the cavity provided for this purpose on a package that is already deep-frozen, and a self-adhesive label is then immediately applied to the indicator, it is proposed to provide the body within the zone of the contacting point for the water with a viscous substance, preferably with a sugar, which upon activation of the indicator prevents the water from flowing upwardly prematurely.

An adhering, transparent plastic foil material, preferably an adhesive chlorotrifluoroethylene foil is used for wrapping the body, namely for all deep-frozen product with the exception of glace, or the wrapping or covering is formed by a shaped plastic object, preferably a deep-drawn part made of transparent PVC, which is used for glace. The path of diffusion of the body is adjusted to the maximum durability of the product to be monitored, preferably at −20° C., and/or the mixing ratio of sodium chloride to citric acid is adjusted to the temperature-dependency of the durability of the product to be monitored. The proposed method and the indicator proposed for carrying out said method are particularly suitable for monitoring the quality or storage condition of deep-frozen foodstuffs within the temperature range of about −25° C. and about +5° C.

BRIEF DESCRIPTION OF THE DRAWINGS

The invention is explained in the following with the help of the drawings of which.

DESCRIPTION OF THE PREFERRED EMBODIMENT

Figure 1:
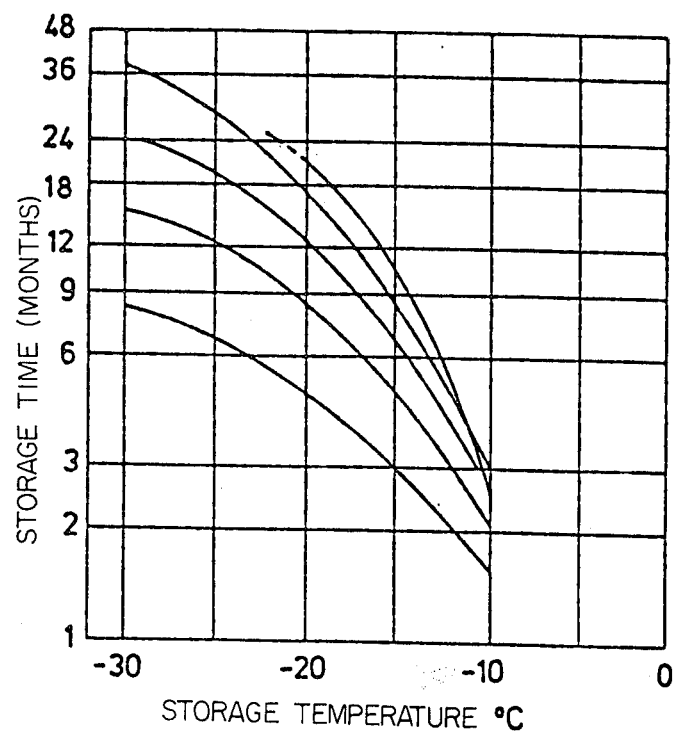
FIG. 1 shows the dependency of the permissible storage duration of different deep-frozen products as a function of their storage temperatures.

The so-called durability curves shown in FIG. 1 were referred to in the discussion of the state of the art. The indicator shown in FIG. 2 comprises a paper strip 1. Said strip of paper is provided with a water-soluble, hydrate-forming substance such as sodium chloride, citric acid, a sugar, cobaltous chloride or with a mixture comprising two or a plurality of said substances. Reference number 2 in FIG. 2 designates the aqueous front which advances by diffusion at diffusion rate "v". The strip 1 is encased by a moisture-tight foil 5 preferably composed of adhesive chlorotrifluoroethylene foil. Said foil leaves a contact point 1a of the strip exposed as shown at 5a by the dashed lines, namely at least on one side. Contact point 1a is thus formed in such a way that it is capable of directly contacting the water reserve of the product, which may be the moisture content of the product itself or an additionally provided water or ice reserve on the product or on its packaging material.

Figure 2:
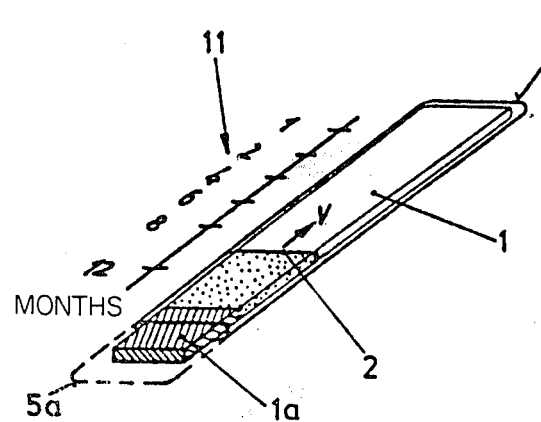
FIG. 2 shows a perspective view of an indicator without color change.

In order to prevent the water starting to diffuse immediately after the contact point 1a has been contacted by water, which is the case if the indicator is applied immediately prior to the freezing of said water reserve, the contact point 1a is provided with a viscous substance, for example with a sugar, which is illustrated in FIG. 2 by the sectioning at point 1a.

Figure 3:
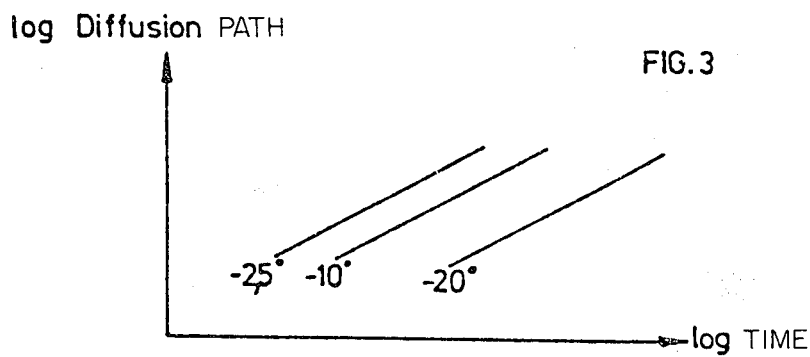
FIG. 3 shows the qualitative dependency of the path of diffusion upon time, on an indicator according to FIG. 2, with the temperature as parameter.

If a few of the indicators of the type specified based on FIG. 2 are each exposed to a different temperature, we obtain the diffusion developments as the function of time as qualitatively shown in FIG. 3, with both the course of diffusion and the time being marked off logarithmically. The temperature values −20° C., −10° C. and −2.5° C. were selected as test temperatures. In the range exceeding 0° C. the rate of diffusion is still significantly higher, because the contact point 1a is in direct contact with water, the cause being that the ice contacted first has melted, so that the water is no longer required to detour by way of the vapor phase. The diagram illustrated in FIG. 3 clearly shows the time which the front of diffusion requires at the individual temperatures in order to travel a defined distance. If the diffusion times so obtained for a predetermined length of path or distance are plotted against the temperature, we obtain curves corresponding with the durability curves of deep-frozen products. Since each deep-frozen product having some amount of moisture can be approximately compared to a block of ice, the function of the flow action is practically independent of the type of deep-frozen product involved, unless the product contains dissolved substances such as sugar, table salt etc. However, on the other hand, the storability does depend on the type of product involved, which means that it is necessary to provide for each type of deep-frozen product a body in conformity with paper strip 1 having a suitably corresponding length, and to adapt the temperature dependence of the diffusion rate to the one of the durability of the product to be monitored by reducing the mixing ratio of the substances, in particular of sodium chloride and citric acid, applied to said strip.

Figure 4:
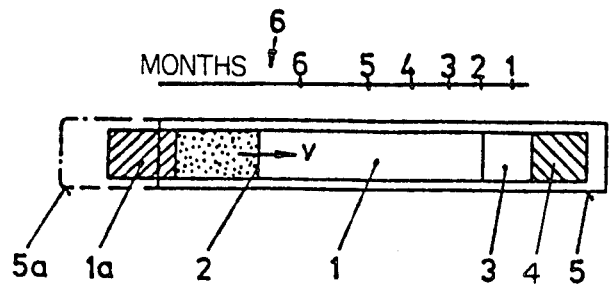
FIG. 4 illustrates a lateral view of another embodiment of the indicator according to FIG. 2 with color change.

The indicator shown in FIG. 4 comprises, in addition to the paper strip 1, the moisture-tight foil 5 and the viscous substance, preferably sugar, applied to contact point 1a, an acid/base indicator disposed at its end opposite contact point 1a, said indicator preferably being a litmus paper 4. A water-soluble acid, preferably citric acid, is applied to paper strip 1. Said acid is dissolved by the water diffusing with front 2 and carried upwardly to reach acid/base indicator 4. Now, in order to avoid a premature color change in acid/base indicator 4 caused, for example by the formation and diffusion of hydrochloric gas, a buffer zone 3 is interconnected in the path between acid/base indicator 4 and contact point 1a. Said buffer area is provided with an acid ampholyte, preferably secondary ammonium citrate and adsorbs undesirable hydrochloric gas by virtue of its basic property. The indicator is furthermore provided with a logarithmic time scale 6, which is related to the remaining durability of the product to be monitored at a specific temperature, for example at $-20°$ C.

The strip-shaped indicator shown in FIGS. 2 and 4 is used particularly in cases in which a mixture of common salt and citric acid is used as the water-soluble, hydrate-forming substance. This is the case with all deep-frozen products with the exception of ice cream. The flow path is relatively long in this case, namely in the order of magnitude of a few centimeters.

Figure 5:
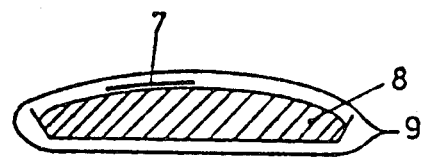
FIG. 5 shows a general view of an indicator applied to the product to be monitored.
Figure 6:
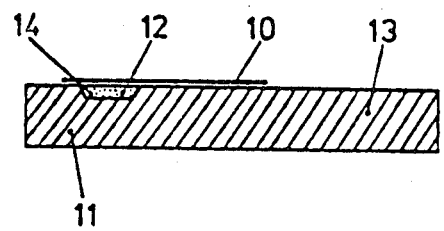
FIG. 6 is a general view of an indicator applied to the packaging material of a product to be monitored.

It is shown in FIG. 5 that said strip-shaped indicator may be attached either directly to the deep-frozen product 8 provided that the product with the indicator is then packaged or wrapped in a plastic foil 9, as this is the case, for example with meats, or it may be attached to a package 11 in the form of a self-adhesive label 10 as shown in FIG. 6, in which case said package is provided with a depression 12 for receiving a small water reserve 14.

Figure 7:
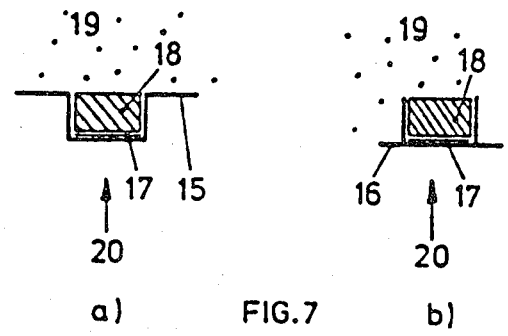
FIG. 7a shows an indicator for glace placed into a recess or cavity made of plastic.
FIG. 7b an indicator for glace inserted in a wall of the packaging material.

The cellulose body formed according to FIGS. 3 and 4 by the strip of paper serving as the diffusion path may, in another embodiment, have a cylindrical or square shape. This shape is used particularly if pure citric acid is used as the water-soluble, hydrate-forming substance, which is the case in the monitoring of ice cream (glace). In this case, the flow path is relatively short, namely only in the order of magnitude of a few millimeters, because citric acid, due to its relatively high viscosity in the liquid state, causes the rate of diffusion to be low. No reaction takes place at temperatures of $-20°$ C. and lower. This indicator, which is shown in FIGS. 7a and 7b, comprises a filter cardboard 18 saturated with citric acid solution and having a cylindrical or square shape. The pills 18, which in this case form the body, are contained in suitable plastic moldings preferably made of polyvinyl chloride (PVC).

According to FIG. 7a, for example, the package for the ice cream or glace to be monitored is provided with a depression projecting outwardly with respect to product 19. Placed into said depression are first an acid/base indicator 17, namely litmus paper, and then the pill 18 saturated with citric acid. FIG. 7b shows a plastic jacket 16 made, for example, of PVC, and attached to the package for the ice cream or glace to be monitored. Said jacket protrudes into product 19 and receives also in this case first an acid/base indicator 17, preferably litmus paper, and subsequently the pill saturated with citric acid. In both embodiments shown in FIGS. 7a and 7b the plastic covering is transparent at least in the area of 20, so that the color change of indicator 17 may be seen from the outside. The product 19, i.e. the ice cream or glace to be monitored, is contacted by pill 18.

The indicators for monitoring the history of time versus temperature of a deep-frozen product as herein specified are particularly suitable for the temperature range of about $-25°$ C. to about $+5°$ C. Said indicators may be adapted to the maximum durability of the deep-frozen product at a specific temperature, preferably at $-20°$ C., by varying the length of the body, while adjustments to the temperature dependence of the durability are made by varying the sodium chloride to citric acid ratio. The indicator may be calibrated or its dependence on temperature may be determined by preparing a flow diagram, plotting the logarithm of the flow time against the logarithm of the diffusion path as shown in FIG. 3. The straight lines so obtained permit good extrapolation.

BEST PROCEDURE FOR IMPLEMENTING THE INVENTION

The indicator according to FIGS. 2 and 4 is manufactured by first saturating a strip of paper with a common salt/citric acid solution and drying said strip subsequently under heat. The one end of said strip is then briefly dipped into a concentrated sugar solution and again dried. The buffer zone 3 is prepared analogously. This component and a piece of litmus paper 4 are then placed in the proper sequence between two strips of a transparent plastic foil or sheet with good adhesive power, preferably an adhesive chlorotrifluoroethylene sheet material. One portion 5a of said foil may be slightly longer so as to slightly overlap the contact area in order to protect said area against loss of moisture to the outside. The embodiment according to FIGS. 7a and 7b is prepared by punching one or a plurality of pills from a filter cardboard material, which was first saturated with citric acid solution and then dried. Said pills are then embedded in cylindrical or square plastic depressions. The litmus indicator is embedded first.

COMMERCIAL UTILIZATION

The specified process and indicator for applying said process offer a suitable and simple and thus inexpensive possibility for monitoring deep-frozen products with respect to their durability, which may be increasingly important in cases of power failure in deep-freezing installations.

I claim:

1. A time temperature integrating indicator for monitoring the history of a deep-frozen product by the diffusion of water along a diffusion path wherein the water front advancement along the diffusion path is a function of elapsed time and of the temperature of the product, the indicator comprising a wick of a material which defines a diffusion path along which water will diffuse; the wick being provided along its diffusion path with citric acid or a mixture of sodium chloride/citric acid or of sodium chloride/sugar, as an absorbing and hydrate forming substance; the formation of the hydrate at least partially providing a visible indication of the water front location; a moisture tight covering enclosing the wick; an opening in the covering for permitting intimate contact between the wick and water on the frozen product, located at the opening in the covering; and additional indicating means for indicating the location of the water front along the diffusion path from the opening in the covering.

2. An indicator according to claim 1, further comprising a viscous substance on the wick in the vicinity of the opening in the covering for preventing premature flow of the water front from the opening along the wick and past the viscous substance.

3. An indicator according to claim 2, wherein the viscous substance is a sugar.

4. An indicator according to claim 1, wherein the absorbing substance is impregnated in the wick.

5. An indicator according to claim 1, wherein the wick is comprised of cellulose material.

6. An indicator according to claim 5, wherein the covering is a plastic molding.

7. An indicator according to claim 5, wherein the cellulose wick has a length selected to give an indication related to the maximum storage life of a product to be monitored by the indicator.

8. An indicator according to claim 7, wherein the wick length is selected to give its indication for a product that is to be stored at $-20°$ C.

9. An indicator according to claim 1, wherein the additional indicating means for indicating the distance of the water front advance comprises a time scale next to the diffusion path to indicate the time elapsed as a function of the advance of the water front, at a predetermined temperature.

10. An indicator according to claim 1, wherein the additional indicating means for indicating the distance of the water front advance comprises an acid/base indicator on the diffusion path away from the opening in the covering for indicating when the water front reaches the acid/base indicator.

11. An indicator according to claim 10, wherein the acid/base indicator is litmus paper.

12. An indicator according to claim 10, wherein the absorbing substance is a sodium chloride/citric acid mixture and the wick comprises a cellulose wick; on the cellulose wick, between the opening in the covering and the acid/base indicator, a buffer substance is provided for absorbing acid gas formed at the wick inside the covering, in order that the gas not reach the acid/base indicator.

13. An indicator according to claim 12, wherein the buffer substance is secondary ammonium citrate.

14. An indicator according to claim 10, wherein the absorbing substance is a sodium chloride/citric acid mixture where the ratio of the mixture is adapted to the temperature dependency of the diffusion rate to be achieved.

15. A method for activating an indicator according to claim 1 comprising the step of contacting the work at the opening in the covering thereover with a water or an ice reserve, which water is one of the water of the product or an additional water reserve at the product.

* * * * *